US00PP19105P3

(12) United States Plant Patent
Jauchen

(10) Patent No.: US PP19,105 P3
(45) Date of Patent: Aug. 19, 2008

(54) MINATURE ROSE PLANT 'PACFIFTYONE'

(50) Latin Name: *Rosa hybrida*
Varietal Denomination: PACfiftyone

(76) Inventor: Daniel Jauchen, Santa Barbara, CA (US)

( * ) Notice: Subject to any disclaimer, the term of this patent is extended or adjusted under 35 U.S.C. 154(b) by 0 days.

(21) Appl. No.: 11/585,270

(22) Filed: Oct. 24, 2006

(51) Int. Cl.
*A01H 5/00* (2006.01)

(52) U.S. Cl. ..... Plt./121
(58) Field of Classification Search ..... Plt./121
See application file for complete search history.

*Primary Examiner*—Kent L. Bell
*Assistant Examiner*—S. B. McCormick/Ewoldt

(57) ABSTRACT

A new miniature rose plant which has abundant, pink colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Botanical Designation: *Rosa hybrida.*
Variety Denomination: 'PACfiftyone'.

BACKGROUND OF THE INVENTION

The present invention constitutes a new and distinct variety of miniature rose plant, which was developed by artificially pollinating an unnamed seedling (not patented) with an unnamed seedling (not patented). The two parents were crossed in the summer of 2004 and the resulting seed was sown in December 2004, in a controlled glasshouse environment. Out of these seedlings one seedling was selected, as the new variety and named 'PACfiftyone'. The new rose may be distinguished from its seed parent, an unnamed seedling, by the following combination of characteristics:

1. 'PACfiftyone' has medium double flowers, while the unnamed seedling has big single flowers.
2. 'PACfiftyone' has pink colored petals, while the unnamed seedling has white petals.

The new variety may distinguished from its pollen parent, an unnamed seedling created by the same inventor, by the following combination of characteristics:

1. 'PACfiftyone', has medium double flowers, while the unnamed seedling has small double flowers.
2. 'PACfiftyone' pink colored petals, wile the unnamed seedling has dark red petals.

BRIEF SUMMARY OF THE INVENTION

Initial asexual reproduction of 'PACfiftyone' by cuttings was first one in Santa Barbara, Calif., USA. This initial and other subsequent propagations conducted in controlled environments have demonstrated that the characteristics of 'PACfiftyone' are true to type and are transmitted one generation to the next. 'PACfiftyone' is a low and compact miniature rose with good vigor. The objective of the hybridization of this rose variety for commercial greenhouse culture was to create a new and distinct variety with:

1. Uniform and abundant flowers with good keepability;
2. Attractive long lasting foliage and compact growth;
3. Year round flowering under glasshouse conditions;

4. Suitability for production from softwood cuttings in pots;
5. Durable flowers and foliage which make the variety suitable for distribution in the floral industry.

This combination of qualities was not present in previously available commercial cultivars of this type, known to the inventor, and distinguish 'PACfiftyone' from all other varieties of which I am aware.

The seeds from hybridization were planted in a controlled environment and evaluations were conducted on the resulting plants. 'PACfiftyone' was selected by, Daniel Jauchen, in his development program in Santa Barbara, Calif., USA.

BRIEF DESCRIPTIONS OF THE DRAWINGS

The accompanying color illustrations show as true as is reasonably to obtain in color photographs of this type, the typical characteristics of the buds, flowers, leaves, stems of 'PACfiftyone'. Specifically illustrated in the drawings:

1: Young shoot.
2: Bud before opening the sepals.
3: Bud at the stage of opening the sepals.
4: Bud at the stage of opening the petals.
5: Flower during course of opening.
6: Open flower — plan view — obverse.
7: Open flower — plan view — reverse.
8: Fully open flower — plan view — obverse.
9: Fully open flower — plan view — reverse.
10: Receptacle showing stamens and pistils.
11: Receptacle showing pistils (stamens and sepals removed).
12: Flower petals, detached — inner surface.
13: Flower petals, detached — outer surface.
14: Bare stem exhibiting thorns and flower attachment.
15: Three leaflets upper side.
16: Three leaflets reverse side.
17: Five leaflets upper side.
18: Five leaflets reverse side.

DETAILED BOTANICAL DESCRIPTION OF THE VARIETY

The following is a detailed description of the Miniature Rose: *Rosa hybrida* 'PACfiftyone'.

The following observations, measurements, values and comparisons describe plants grown in glass houses in Santa Barbara, Calif. USA. The age of the observed plants were 3 months after propagation by cuttings, and produced as flowering pot plants in container of 10 centimeter in diameter. Environmental conditions in the cultivation area for the observed plants, has been temperatures from 64 to 78 degree Farenheit, and 10 to 20 hours day length with assimilation light. Light levels from 600 foot candles to 6000 foot candle. The relative humidity has been ranging from 50 to 85%. Color references are made using The Royal Horticultural Society (London, England) Colour Chart, 1995, except where common terms of color are used. For a comparison, the nearest existing rose variety is 'POULrolyt', a rose variety described and illustrated in U.S. Plant Pat. No. 13,138. Chart 1 details several physical characteristics of 'PACfiftyone' and 'POULrolyt'.

CHART 1

| | 'PACfiftyone' | 'POULrolyt' |
|---|---|---|
| Petal color, Upper surface | Red Group 49A | Red Group 50A |
| Petal color, Reverse surface | Red Group 49A | Red-Purple Group 58B |
| Petal count | 45 to 50 | 30 to 35 |

Parents: Unnamed seedling times unnamed seedling.

Classification:

*Botanical.*—*Rosa hybrida.*

*Commercial.*—Miniature.

Plant:

*Plant growth.*—Moderately vigorous. Grows compact upright to bushy. When grown as 10 cm pot plant, the average height of the plant itself is 18 cm to 20 cm, and average widths is 20 cm. When grown as a 15 cm pot plant, the average height of the plant itself is 22 cm to 27 cm, and average width is 30 cm.

Stem:

*Color.*—Young wood: Yellow-Green Group 137B. Older wood: Green Group between 137A and 137B.

*Thorns.*—Incidence: 40 to 50 per stem. Size: 1 to 4 mm. Form: Deep concave. Color: Greyed-Purple Group 185B.

*Surface.*—Young wood: Smooth. Older wood: Smooth.

*Stem diameter.*—2 mm to 3 mm.

*Internode length.*—25 mm to 35 mm.

*Numbers of internodes.*—7 to 8.

Plant foliage: Leaves arranged alternately, compound with 3 to 5 leaflets per leaf, generally symmetrical, abundant, and flat in aspect. Stipules at petiole base.

*Quantity of leaves.*—7 to 8 per lateral branch.

*Leaf size.*—Length 45 mm to 85 mm, width 35 mm to 50 mm.

*Petioles.*—Color: Green Group 136B, with intonations of Greyed-Purple Group 185B. Margins: Entire. Length: 10 mm to 15 mm. Diameter: about 0.5 mm to 1 mm.

*Stipules.*—Size: Length 2 mm to 4 mm, width 1 mm to 2 mm. Surface: Smooth. Color for upper surface: Green Group 136A, with intonations of Greyed-Purple Group 185B. Color for lower surface: Green Group 136B. Margins: Entire.

*Rachis.*—Color: Green Group 136B, with intonations of Greyed-Purple Group 185B. Margins: Entire. Length: 15 mm to 45 mm. Diameter: 0.5 mm to 1 mm.

*Leaflets.*—Edge: Serrated. Serration: Single. Shape: Ovate with acute apex and obtuse base. Texture: Smooth. Appearance: Dull. Size: Length: 10 mm to 35 mm, width: 5 mm to 20 mm. Color: Young foliage: Upper surface: Green Group 136A. Lower surface: Green Group 137B, wit intonations of Greyed-Purple 185B. Color: Mature foliage: Upper surface: Green Group 136A. Lower surface: Green Group 137B. Leaf vein color: Upper surface: Green Group 136A. Reverse surface: Green Group 138D.

Inflorescence:

*Blooming habit.*—Recurrent.

*Number of flowers.*—Generally one to four buds per flowering stem.

*Peduncle.*—Color: Green Group between 137B and 137D. Texture: Smooth. Length: 40 mm to 60 mm Diameter: 1 mm to 2 mm. Strength: Upright.

*Receptacle.*—Surface: Smooth, glabrous. Shape: Funnel-shaped. Size: height 5 mm to 6 mm, width 5 mm to 6 mm. Color: Green Group 138B.

*Sepals.*—Quantity: Five. Shape: Narrowly ovate with acute tip. Texture: Leathery. Margin: Foliaceous appendages on three of the five sepals. Appearance: Dull. Color: Upper surface: Green Group 136A. Reverse surface: Green Group between 138A and 138C. Size: Length 20 mm to 25 mm, width 3 to 5 mm.

*Buds.*—Size: Height 15 mm to 20 mm, diameter 10 mm to 14 mm, Upon opening. Shape: Cupped to ovoid. Color: at ¼ opening, Red Group 49A.

*Flower.*—Duration: As a pot plant, flowers last from 15 to 18 days. Fragrance: Slightly perfume. Size: 40 mm to 45 mm in diameter. Depth: 15 mm to 20 mm. Form: Shape of flower when viewed from the side: Upon opening: cupped to ovoid. Open flower: Flat. Color: Petals, upon opening: Upper surface: Outer petals Red Group between 39A and 39B, with Intonations of White Group 155D. Base in White Group 155D. Inner petals Red Group 38A, base in Yellow Group 13A. Reverse surface: Outer petals Red Group between 39A and 39B, with Intonations of White Group 155D. Base in White Group 155D. Inner petals Red Group 38A, base in Yellow Group 13A. Petals after opening: Upper surface: Outer petals Red Group between 39A and 39B, with Intonations of White Group 155D. Base in White Group 155D. Inner petals Red Group 38A, base in Yellow Group 13A. Reverse surface: Outer petals Red Group between 39A and 39B, with intonations of White Group 155D. Base in White Group 155D. Inner petals Red Group 38A, base in Yellow Group 13A. General tonality: On open flower: Third day: Red Group 49A. Afterwards: Red Group between 49A and 49B.

*Petals.*—Petal reflex: Outermost petals reflex backwards at opening. Fully open all petals reflex backwards.

*Texture.*—Smooth.

*Petal edges.*—Entire.

*Petal count.*—45 to 50 on the average per flower.

*Petal size.*—Length 20 mm to 22 mm, width 10 mm to 20 mm.

*Shape.*—Outer petals: Round — ovate. Inner petals: Ovate. Apex: Rotundate. Base: Obtuse to rotundate.

*Petaloids.*—None.

*Reproductive organs.*—Stamen number: Approximately 34 to 40 on average per flower.

*Stamens length.*—6 mm to 7 mm.

*Pollen.*—Color: Greyed-Orange Group 167B. Abundance: Heavy.

*Anthers.*—Size: 1 mm to 1.5 mm. Color: Greyed-Orange Group 167B. Shape: Oblong.

*Filaments.*—Size: 5 mm to 6 mm. Color: Yellow Group 13A.

*Pistils number.*—Approximately 35 to 40 on average per flower.

*Stigmas.*—Location: Protrude less than the anthers. Color: Green-White Group 157A.

*Styles.*—Color: Yellow-White Group 158C. Length: 3 mm to 4 mm.

Development:

*Vegetation.*—Dense.

*Blooming.*—Abundant.

*Aptitude to bear fruit.*—Poor.

*Resistance to disease.*—Above average resistance to mildew and Botrytis under normal growing conditions in Santa Barbara, Calif., USA. Hips/seeds has not been observed due to that the plant has never been grown to the stage of seed development, due to the fact, that the variety is developed for use as a flowering pot plant only.

*Winter hardiness & drought/heat tolerance.*—Due to the fact, that is variety is a potted flowering plant, developed indoor use only, the plant is not tested for winter hardiness or drought/heat tolerance.

What is claimed is:

1. A new and distinct variety of Rose plant of the miniature class, substantially as herein illustrated and described as a distinct and novel rose variety due to its abundant pink flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

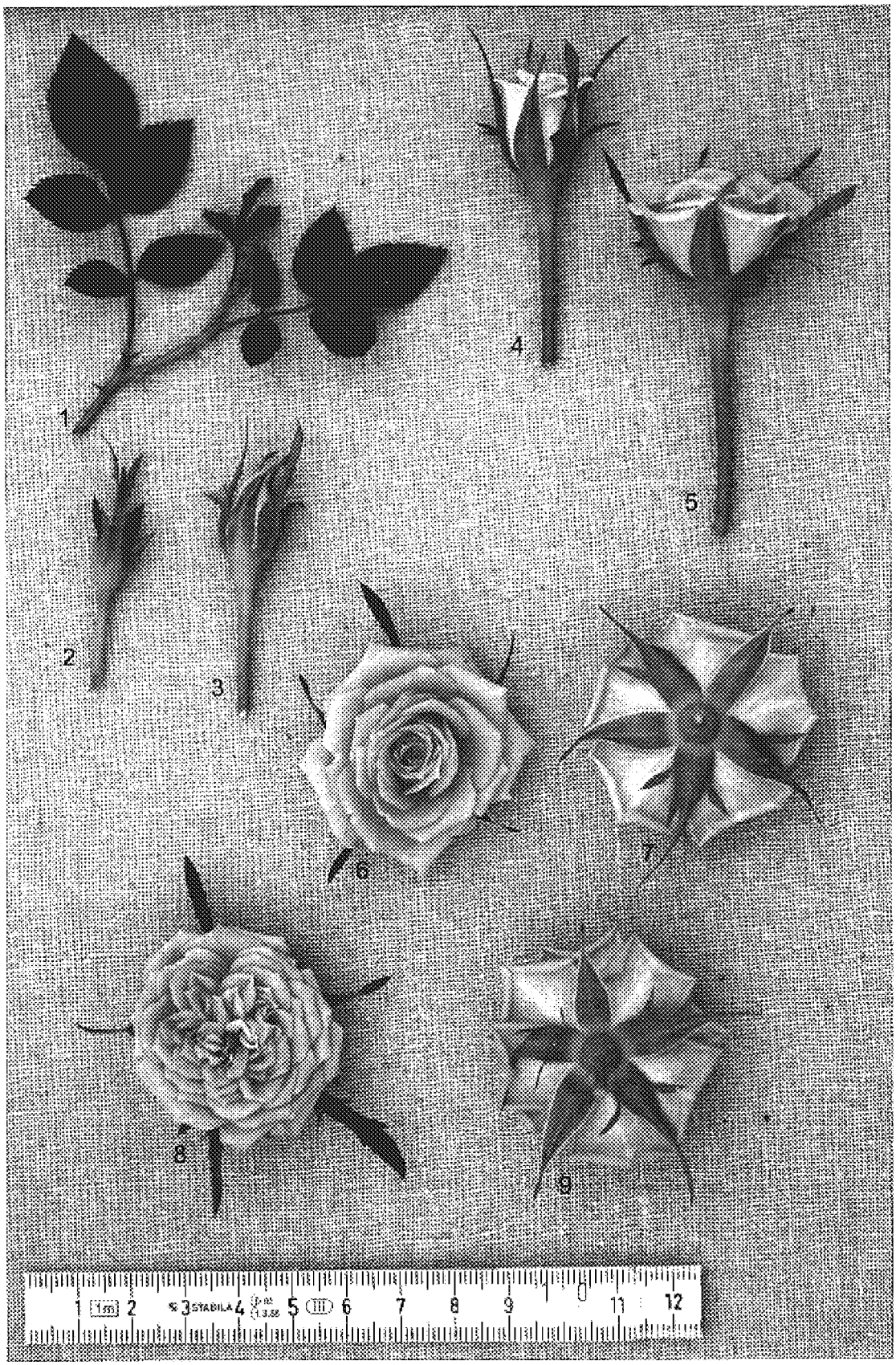
1
2
3
4
5
6
7
8
9

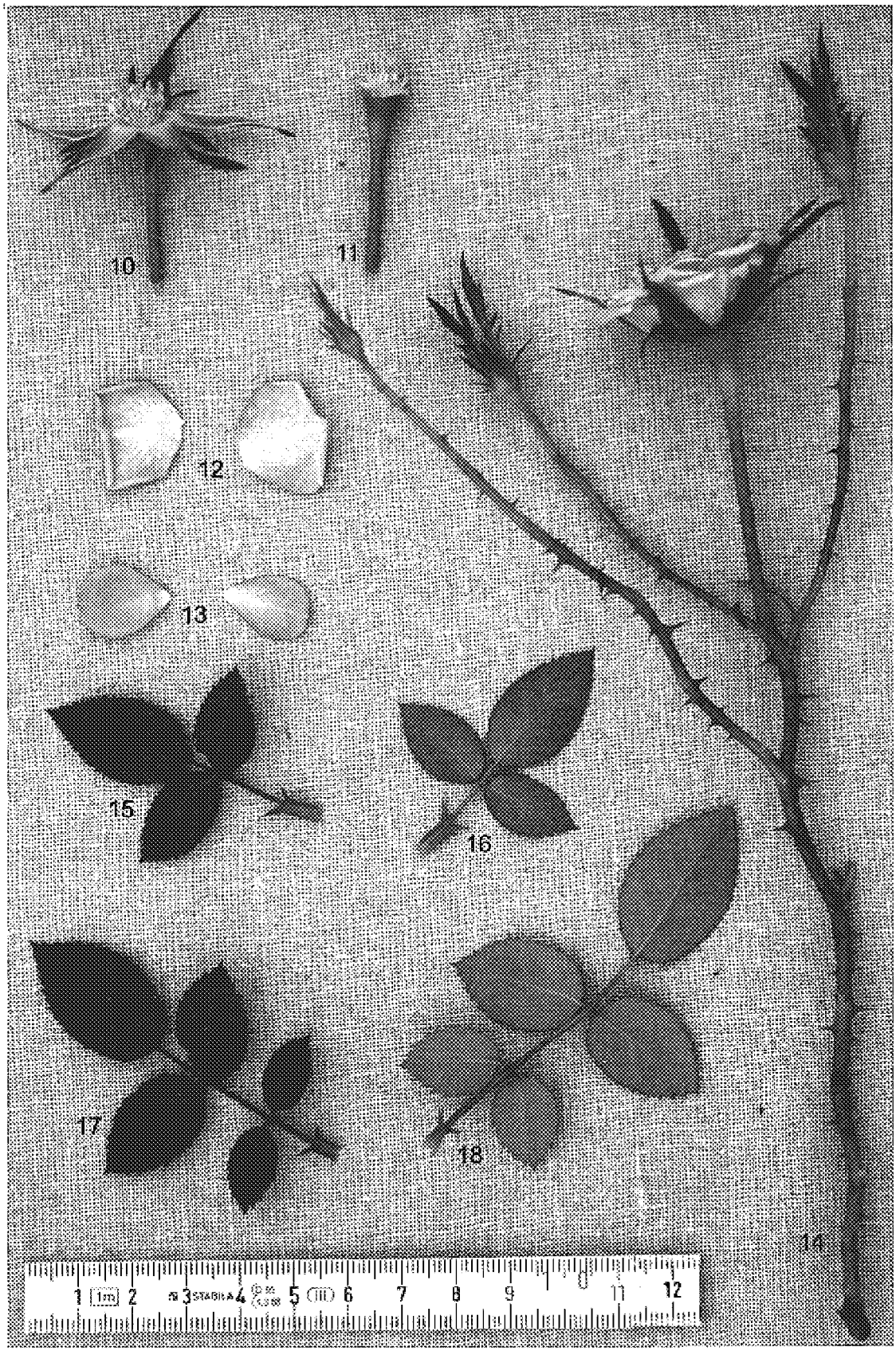
10
11
12
13
14
15
16
17
18